United States Patent [19]

Arntz et al.

[11] Patent Number: 5,364,984
[45] Date of Patent: Nov. 15, 1994

[54] PROCESS FOR THE PREPARATION OF 1,3-PROPANEDIOL BY THE HYDROGENATION OF HYDROXYPROPIONALDEHYDE

[75] Inventors: Dietrich Arntz, Oberursel; Thomas Haas, Rüsselsheim; Adolf Schäfer-Sindlinger, Frankfurt, all of Germany

[73] Assignee: Degussa Aktiengesellschaft, Frankfurt, Germany

[21] Appl. No.: 948,718

[22] Filed: Sep. 24, 1992

[30] Foreign Application Priority Data

Oct. 1, 1991 [DE] Germany .............................. 4132663

[51] Int. Cl.$^5$ .................. C07C 31/20; C07C 29/141; B01J 23/42
[52] U.S. Cl. ...................................... 568/862
[58] Field of Search ......................... 568/862

[56] References Cited

U.S. PATENT DOCUMENTS

| | | | |
|---|---|---|---|
| 2,434,110 | 1/1948 | Hatch et al. | 260/602 |
| 3,536,763 | 10/1970 | Eleuterio et al. | 260/602 |
| 4,113,660 | 9/1978 | Abe et al. | 502/340 |
| 4,524,225 | 6/1985 | Qualeatti et al. | 568/885 |
| 4,929,586 | 5/1990 | Hegedus et al. | 502/309 |
| 4,933,473 | 6/1990 | Ninomiya et al. | |
| 5,015,789 | 5/1991 | Arntz et al. | 568/862 |

FOREIGN PATENT DOCUMENTS

| | | |
|---|---|---|
| 343475 | 11/1989 | European Pat. Off. |
| 412337 | 2/1991 | European Pat. Off. |
| 3926136 | 2/1991 | Germany |

OTHER PUBLICATIONS

"Highly Dispersed Metallic Oxides Produced by the Aerosil Process", *Technical Bulletin Pigments*, No. 56, Nov. 1990.

*Primary Examiner*—Johann Richter
*Assistant Examiner*—Rebecca Cook
*Attorney, Agent, or Firm*—Beveridge, DeGrandi, Weilacher & Young

[57] ABSTRACT

Disclosed is a process for the preparation of 1,3-propanediol by the hydrogenation of hydroxypropionaldehyde (HPA) in aqueous solution on a formed carrier catalyst in a solid bed, the concentration of HPA in the solution being from 5 to 100% by weight and hydrogenation being carried out at temperatures of from 30° to 180° C. and hydrogen pressures of from 5 to 300 bar and at a pH of from 2.5 to 6.5. The carrier catalyst is formed principally of titanium oxide on which platinum is applied in a finely divided form in a quantity of from 0.1 to 5.0% by weight, based on the carrier.

13 Claims, 2 Drawing Sheets

5,364,984

PROCESS FOR THE PREPARATION OF 1,3-PROPANEDIOL BY THE HYDROGENATION OF HYDROXYPROPIONALDEHYDE

BACKGROUND AND INTRODUCTION

The present invention relates to a process for the preparation of 1,3-propanediol by the hydrogenation of hydroxypropionaldehyde (HPA) in aqueous solution on a fixed bed catalyst. In a further aspect, the invention also concerns a catalyst used for the hydrogenation of HPA.

1,3-Propanediol has many different possibilities of application as a monomer unit for the formation of polyesters and polyurethanes and as starting material for the synthesis of cyclic compounds. Various processes are known for the preparation of 1,3-propanediol. These either start from a molecular structure of a $C_2$- and $C_1$-unit or from a $C_3$-unit such as acrolein. When acrolein is used, it is first hydrated in the presence of an acid catalyst to form hydroxypropionaldehyde. The aqueous reaction mixture formed in the process of hydration still contains about 8% of oxaheptanedial in addition to about 85% of HPA and other organic components in minor proportions by weight after removal of unreacted acrolein. This reaction mixture is hydrogenated in the presence of hydrogenation catalysts to produce 1,3-propanediol.

According to U.S. Pat. No. 2,434,100, catalysts containing one or more hydrogenation active metals such as Fe, Co, Ni, Cu, Ag, Mo, W, V, Cr, Rh, Pd, Os, Ir or Pt are suitable for the hydrogenation of HPA to 1,3-propanediol.

As described in German patent 39 26 136.0, the catalyst may be used as such in suspended form or bound to a carrier or form part of fixed bed catalysts. Homogeneous catalysts may also be used. Raney nickel, which may be doped with various other catalytically active metals, platinum on active charcoal, and platinum on aluminum oxide are known as suspension catalysts (from U.S. Pat. No. 3,536,763). A high volume/time yield of hydrogenation is obtained if the solution to be hydrogenated is at a pH of from 2.5 to 6.5, the hydrogenation temperature is in the region of from 30° to 180° C., and hydrogen pressures of from 5 to 300 bar are employed.

Nickel catalysts are mainly used for hydrogenation. Among these, fixed bed catalysts are preferred as they do not need to be filtered off after hydrogenation. Nickel on $Al_2O_3/SiO_2$ is an example of a typical fixed bed catalyst for this purpose.

Catalytic hydrogenation entails the risk of small quantities of the catalytically active element being discharged with the stream of product in the form of soluble compounds so that additional operating steps are then necessary to remove these impurities. This phenomenon is most marked in the case of suspension catalysts such as Raney nickel, but nickel fixed bed catalysts also entail the risk of contamination of the product with nickel compounds, albeit in very small quantities.

Hydrogenation processes may be characterized by the conversion rates, selectivities and volume/time yields obtainable by these processes. The conversion rate indicates how many mols of the educt (in this case HPA) are converted into other substances by hydrogenation. The figure is usually given in percent of the mols of educt put into the process:

$$\text{Conversion of HPA (\%)} = \frac{\text{mols of HPA converted}}{\text{mols of HPA supplied}} \times 100$$

The selectivity of the hydrogenation process, on the other hand, is a measure of the number of mols of converted educt which are converted into the desired product:

$$\text{Selectivity (\%)} = \frac{\text{mols of 1,3-propanediol}}{\text{mols of HPA converted}} \times 100$$

For continuous hydrogenation processes the volume/time yield is another important characteristic which indicates the quantity of product obtainable per unit time and volume of reactor.

In large scale technical hydrogenation of HPA to 1,3-propanediol it is important for the economical efficiency of the hydrogenation process and the quality of the product that the conversion rate and selectivity should be close to 100%. Although the water present in the stream of product as well as residues of HPA and by-products are removed from the propanediol by distillation after hydrogenation, this distillative separation is rendered very difficult by the residue of HPA and by-products and may even become impossible due to reactions between the HPA residue and propanediol to form acetals, whose boiling point is close to the boiling point of propanediol. The lower the conversion rate and the selectivity, the poorer the quality of product obtainable.

Conversion rate, selectivity and volume/time yield are influenced by the properties of the catalyst and by the conditions of hydrogenation such as the reaction temperature, the hydrogen pressure, and the length of hydrogenation time, or, in the case of continuous hydrogenation, by the liquid hourly space velocity.

When HPA is hydrogenated to propanediol, it is observed that the main reaction has a linear relationship to the hydrogen pressure and the time (liquid hourly space velocity in the case of continuous processes), whereas the reaction temperature has hardly any influence.

The formation of by-products, on the other hand, is exponentially dependent upon the temperature. Other conditions being equal, the formation of by-products is doubled with every 10° C. rise in temperature, with the result that the reaction becomes progressively less selective. An increase in the hydrogen pressure, on the other hand, has a positive effect on the selectivity. However, the positive influence of pressure on the selectivity is less powerful than the negative effect of a rise in temperature since the hydrogen pressure increases the velocity of the main reaction only linearly while an increase in temperature increases the velocity of the side reaction exponentially.

One important criterion of the quality of the catalysts used for the hydrogenation process is their service life in operation, i.e., good catalysts should ensure a constant conversion rate and selectivity in the hydrogenation of HPA to propanediol in the course of the operating time. In this respect hydrogenation processes known in the art, in particular those based on nickel catalysts, are found to have insufficient long term stability. As a result, more frequent changes in the whole catalyst package are required, with the well-known attendant problems of elimination of impurities and working up of the compounds containing nickel.

SUMMARY OF THE INVENTION

An object of the present invention is to provide a hydrogenation process which is free from the above-mentioned disadvantages of processes known in the art and is particularly distinguished by improved long-term stability.

According to the present invention, this and other objects are achieved by a process for the preparation of 1,3-propanediol by the hydrogenation of hydroxypropionaldehyde (HPA) in aqueous solution on a formed special carrier catalyst in a fixed bed. A feature of the invention resides in the carrier catalyst which consists essentially of titanium oxide carrying platinum in a finely divided form in a quantity of from 0.1 to 5.0% by weight, based on the carrier.

DETAILED DESCRIPTION OF THE INVENTION

Figure 1:
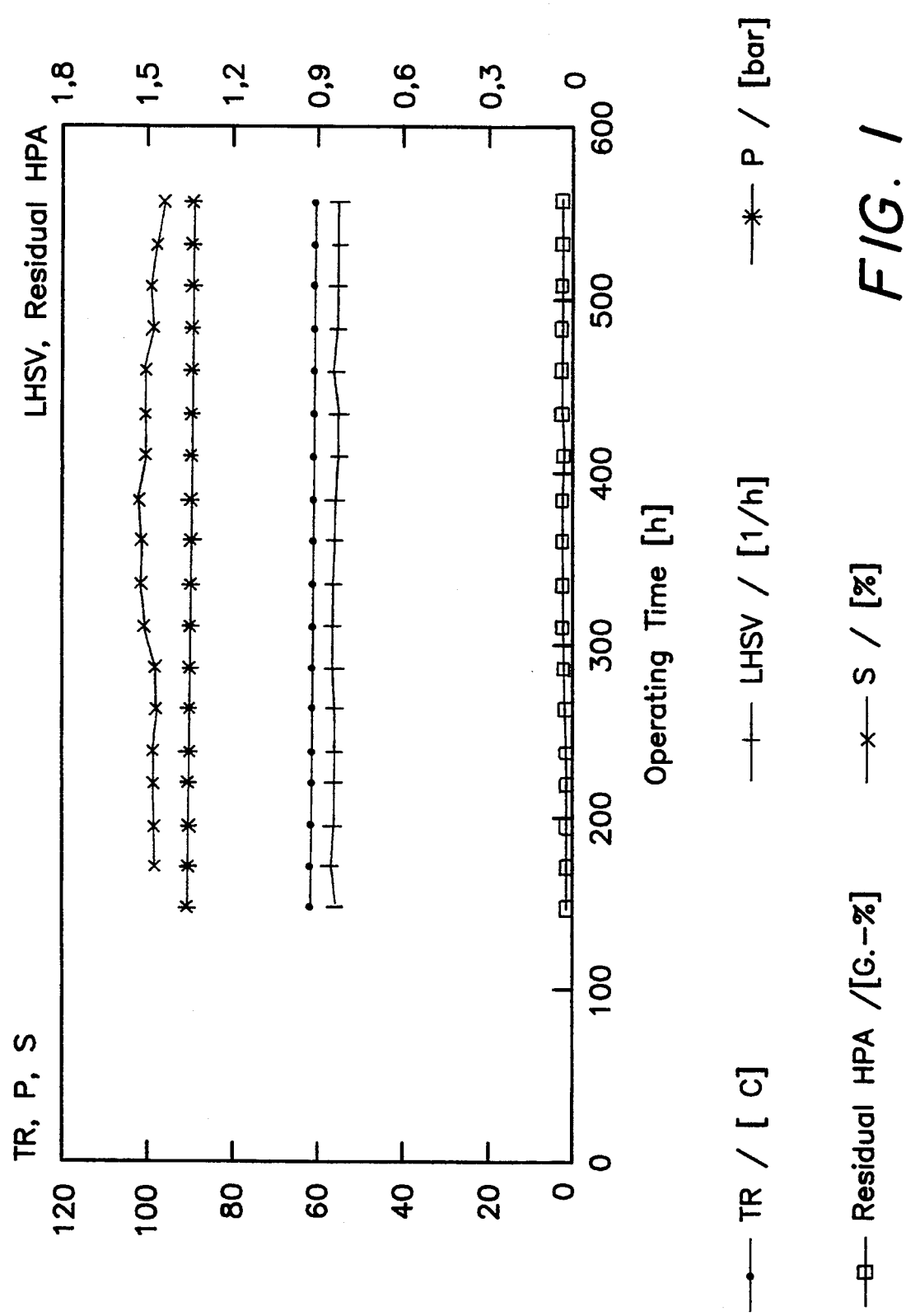
FIG. 1: Represents the long term performance of a hydrogenation process according to the invention using $Pt/TiO_2$ catalysts.

In one particularly advantageous embodiment of the invention, the titanium oxide used is a so called pyrogenic titanium oxide obtained from titanium tetrachloride by flame hydrolysis and having a BET surface area of from 40 to 60 m$^2$/g, a total pore volume of from 0.25 to 0.75 ml/g, an average primary particle size of 20 nm, a density of 3.7 g/cm$^3$ and an X-ray structure of from 20 to 40% rutile and 80 to 60% anatase. Its impurities of silicon dioxide, aluminum oxide and iron oxide amounting to less than 0.5% by weight. Pyrogenic titanium oxide such as P25 of Degussa AG is particularly suitable as carrier for the catalytically active component; it has a high specific surface area according to BET within the above range, amounting to, on average, 50 m$^2$/g (determined according to DIN (German Industrial Standard) 66131).

The pyrogenic titanium oxide is processed into shaped particles such as pellets, granulates, or extrusion moulded particles and is then impregnated with the required quantity of platinum, preferably using a soluble platinum compound (preferably hexachloroplatinic acid), and subsequently dried and reduced in a stream of hydrogen for 1 to 10 hours at temperatures from 250° to 500° C. This preparation provides a fine subdivision of the platinum on the catalyst carrier, with crystallite sizes of from 1 to 10 nm, and a carbon monoxide adsorption of from 0.5 to 1.6 ml of CO/g of catalyst. Other platinum compounds are also suitable for impregnation, e.g., tetraaminoplatinum(II) nitrate, tetraaminoplatinum(II) hydroxide, or tetraaminoplatinum(II)-chloride-1-hydrate.

One particular advantage of the process according to the invention is the unexpected improved service life of the catalyst compared with those used in conventional processes for the hydrogenation of 1,3-propanediol. Moreover, unexpectedly no loss of platinum due to discharge with the stream of product can be ascertained within the limits of accuracy of measurement even after several hundred hours operation in a trickling bed. This proves that the platinum is very firmly fixed on the titanium oxide carrier.

The invention will now be illustrated with the aid of some examples.

EXAMPLES

In these examples, standard $Ni/Al_2O_3/SiO_2$ catalysts are compared with the catalysts used according to the present invention as regards conversion rate and selectivity in batch processes and long term performance in a trickling bed.

The $Ni/Al_2O_3/SiO_2$ catalysts used for comparison with the state of the art were of the "Girdler G134ARS" type of Südchemie Company containing about 30–40% by weight of nickel oxide. They were used in the form of extrusion moulded particles 1.5 mm in diameter and 1 to 3 mm in length.

To characterize the catalyst carriers and the impregnated catalysts, the specific BET surface area of the carriers and their pore radii distribution were determined after the carriers had been calcined. After impregnation of the carriers with suitable platinum compounds and reduction of these compounds substantially to metallic platinum, the active metal surface was determined by measurements of CO adsorption.

Determination of the specific surface area is standardized in DIN 66131. Pores are divided into micropores having diameters below 2 nm, mesopores having diameters from 2 to 50 nm, and macropores having diameters greater than 50 nm. The volume of the micropores is determined by the nitrogen adsorption and evaluation according to the process of Brunauer, Emmett and Teller (BET). The nitrogen adsorption method of De Boer is used for determining the mesopores. The macropores are determined by means of mercury porosometry.

Carbon monoxide adsorption is used as a measure of the active metal surface of the finished catalysts. This value gives information on the quality of the metal dispersion. The particle size distribution of the metal crystallites may be determined directly by an additional transmission electron microscopic (TEM) investigation.

Preparation of the $Pt/TiO_2$ catalysts

So-called pyrogenic titanium oxide of Degussa (TiO$_2$-P25) obtained from titanium tetrachloride by flame hydrolysis was used for the preparation of the catalyst carriers. This material has a specific surface area (BET) of 48 m$^2$/g and a total pore volume of 0.33 ml/g composed of 0.27 ml/g of mesopores and 0.06 ml/g of macropores. The pyrogenic titanium oxide consists of about 30% of rutile and about 70% of anatase. Its primary particles have an average size of about 20 mm.

Part of this material was used immediately and another part was used after several hours tempering at temperatures above 600° C. (e.g., 950° C. for 12 hours). Tempering completely converted the crystal structure of the titanium oxide material into rutile. The specific BET surface area was reduced to values below 13 m$^2$/g (the ultimate minimum would be 0 m$^2$/g for a bulk rutile crystal). In the following examples the untempered material is referred to as pyrogenic titanium oxide (pyrog. TiO$_2$) and the tempered material as tempered titanium oxide (temp. TiO$_2$).

A) Preparation of the granulate 1000 g of Titanium oxide P25 of Degussa were introduced in the untempered state into a granulation container (Eirich mixer, Eirich Company) and granulated with slow addition of a total of 350 ml of completely salt-free water. During the granulating process the temperature in the mixture rose from room temperature to 50° C. Granulation was terminated after about 9 minutes and the granulate was then dried in a rotary tubular furnace at 200° C. until dry.

B) Preparation of extrusion moulded particles 1000 g of Titanium oxide P25 of Degussa were introduced in the untempered or tempered state into a kneading extruder (Werner and Pfleiderer) together with 5 litres of completely salt-free water and briefly kneaded until the water and titanium oxide were homogeneously mixed. 10 g of Tylose (MH 1000, Fluka) dissolved in 200 ml of completely salt-free water were then added. The mixture was kneaded for one hour until a plastic mass was obtained. The mass was then extruded to form particles having a diameter of 1.6 mm and a length of about 10 mm, which were dried in a drying cupboard at 110° C. for about 12 hours. After drying, the particles were calcined in a hot air tempering oven at 400° C. for one hour.

When pyrogenic titanium oxide was used, the finished extrusion moulded particles and the granulates had a BET surface area of 48 $m^2g$ and a total pore volume of 0.33 ml/g composed of 0.27 ml/g of mesopores and 0.06 ml/g of macropores. No micropores could be found within the accuracy of measurement. Working up of the pyrogenic $TiO_2$ starting material into shaped particles thus produced virtually no change in the properties (e.g., its specific surface area and pore volume) of the titanium oxide; thus the ranges given above for BET surface area, total pore volume, average primary particle size, and density for pyrogenic titanium oxide should be similar for the shaped particles. The shaped particles of tempered titanium oxide had a specific surface area below 13 $m^2/g$ after the shaping process, like the starting material.

The catalyst carriers thus produced were impregnated by the so-called Incipient-Wetness-Method. For this process, which is known in the art, the maximum water absorption capacity of the carrier was first determined in the known manner and a solution of hexachloroplatinic acid whose volume amounted to about 95% of the maximum absorption of the given quantity of catalyst carrier was then prepared and its platinum content was adjusted to the desired platinum content of the finished catalyst. The pH of the solution was adjusted to 4 by the addition of hydrochloric acid and the solution was then evenly distributed over the catalyst carrier. When the total quantity of solution had been absorbed, the impregnated particles were first predried in a vacuum drying cupboard at 70° C. and 150 mbar for one hour and drying was then completed at 24 mbar for a further 2 hours.

After impregnation, the catalyst carriers contain homogeneously distributed crystals of hexachloroplatinic acid. These were reduced to metallic platinum in a stream of hydrogen to activate the catalysts. For this purpose, the impregnated carriers were heated to 230° C. under a stream of nitrogen. When a temperature of 230° C. was reached, the stream of nitrogen was replaced by a stream of hydrogen. The reaction which set in was distinctly exothermic so that the temperature during the reduction rose to about 280° C. The material was cooled to 100° C. after about one hour, and nitrogen was passed over the catalyst until it reached room temperature.

ESCA (electron spectroscopy for chemical analysis) and SIMS (secondary ion mass spectroscopy) investigations were carried out on the finished catalysts with 2% by weight of platinum. The tests showed that as the reaction time increases, platinum is obtained as Pt(O), i.e., in metallic form. The proportion of Pt(II) decreases from 25% after one hour's reduction to 14% after 10 hours' reduction. TEM investigations showed homogeneous distribution of platinum crystals measuring from 2 to 5 nm. CO adsorption measurements yielded a value of 1.66 ml of CO/g of catalyst.

EXAMPLE 1

Comparison of the activities of $Ni/Al_2O_3/SiO_2$ catalysts with Pt catalysts to be used according to the present invention on pyrogenic $TiO_2$ carriers in the batchwise hydrogenation of HPA in autoclaves.

Nickel fixed bed catalysts (Girdler G134ARS of Südchemie) were compared with Pt catalysts on pyrogenic $TiO_2$ carriers to be used according to the present invention for their activity in batchwise hydrogenation of HPA solution. For comparison, the catalysts to be used according to the present invention were used in granulate form with a noble metal charge of 2% by weight of platinum on pyrogenic titanium oxide. The conversion rate and the selectivity were determined in each case.

The hydrogenations were in detail carried out as follows: 23.5 g of catalyst corresponding to a substrate to catalyst ratio of 400:1 were weighed into the previously prepared catalyst basket in a 2 litre Hastelloy autoclave equipped with gassing stirrer and means for liquid agitation.

The autoclave was then evacuated, 750 ml of HPA solution having a particular molar content of HPA were sucked in and gaseous hydrogen was introduced until a pressure of 150 bar was obtained. After the stirrer had been switched on, the autoclave was first heated to 50° C. for 15 minutes. The reaction which set in was found to be slightly exothermic so that hydrogenation took place at about 60°–65° C. The change in temperature and pressure was checked every 15 minutes during the reaction. Hydrogenation was stopped after 4 hours.

Table 1 shows the values for conversion and selectivity obtained after this time. Column 4 shows the mol of HPA contained in the aqueous educt solution. 0.94 Mol of HPA in 750 ml of aqueous solution corresponds to a proportion by weight of HPA of about 10%. Column 5 shows the quantity of the 1,3-propanediol produced in mols. The nickel comparison catalyst known from the art (referred to as "V" in Table 1) converts the total quantity of HPA put into the process but its selectivity is poor. Only 74.5% or 86.3% of the number of mols of HPA put into the process are converted into 1,3-propanediol. The catalyst on pyrogenic $TiO_2$ carrier to be used according to the invention (referred to as "K1" in Table 1), on the other hand, unexpectedly has excellent selectivity. In Table 1-3, the column for HPA contains the values of the HPA supplied; the converted HPA is not given but can be calculated from the HPA values and conversion values.

TABLE 1

| Cat | Metal | Carrier | HPA [mol] | 1,3-PD [mol] | Conversion [%] | Selectivity [%] |
|---|---|---|---|---|---|---|
| V | Ni | $Al_2O_3/SiO_2$ | 0.94 | 0.70 | 100 | 74.5 |
| V | Ni | $Al_2O_3/SiO_2$ | 0.73 | 0.63 | 100 | 86.3 |
| K1 | Pt(2%) | pyrog.$TiO_2$ | 0.94 | 0.88 | 97.9 | 95.6 |
| K1 | Pt(2%) | pyrog.$TiO_2$ | 0.77 | 0.76 | 100 | 98.7 |

$H_2$ pressure: 150 bar; T = 60–65° C.

EXAMPLE 2

Comparison of different Pt contents on pyrogenic $TiO_2$ carriers.

To investigate the dependence of the catalytic activity of the catalysts to be used according to the present invention on the Pt content, the pyrogenic titanium oxide carriers were prepared with differing platinum charges. Test hydrogenations carried out in the Hastelloy autoclave corresponding to Example 1 produced the results shown in Table 2. The selectivity and conversion rates increased with increasing platinum content.

TABLE 2

| Cat | Metal | Carrier | HPA [mol] | 1,3-PD [mol] | Conversion [%] | Selectivity [%] |
|---|---|---|---|---|---|---|
| K3 | Pt(0.5%) | pyrog.$TiO_2$ | 0.774 | 0.705 | 98.9 | 92.2 |
| K2 | Pt(1.0%) | pyrog.$TiO_2$ | 0.770 | 0.73 | 98.7 | 96.0 |
| K1 | Pt(2.0%) | pyrog.$TiO_2$ | 0.770 | 0.76 | 100.0 | 98.7 |

$H_2$ pressure: 150 bar; T = 60–65° C.

EXAMPLE 3

Comparison of different Pt contents on tempered $TiO_2$ carriers.

The investigations in Example 3 were carried out analogously to those of Example 2. The only difference lay in the use of tempered titanium oxide instead of pyrogenic titanium oxide. The results are shown in Table 3.

TABLE 3

| Cat | Metal | Carrier | HPA [mol] | 1,3-PD [mol] | Conversion [%] | Selectivity [%] |
|---|---|---|---|---|---|---|
| K4 | Pt(0.5%) | tempered $TiO_2$ | 0.508 | 0.477 | 99.8 | 94.1 |
| K5 | Pt(1.0%) | tempered $TiO_2$ | 0.503 | 0.476 | 99.6 | 95.1 |
| K6 | Pt(2.0%) | tempered $TiO_2$ | 0.508 | 0.475 | 99.2 | 94.3 |

$H_2$ pressure: 150 bar; T = 60–65° C.

In batchwise hydrogenation, catalysts K4 to K6 based on tempered titanium oxide produced similar results to catalysts K1 to K3 based on pyrogenic titanium oxide, but with repeated use they showed a distinct decrease in conversion and selectivity compared with the catalysts on pyrogenic carriers.

EXAMPLE 4

Long term performance of Pt catalysts on pyrogenic titanium oxide carriers in a trickling bed A trickling bed installation having a reactor volume of 1.3 litres was used for the continuous hydrogenation in a trickling bed (Kirk-Othmer Encyclopedia of Chemical Technology, Third Edition, Volume 19, pages 880–914 (especially page 884) are incorporated by reference). The installation consisted of a liquid receiver, a preheating station, the fixed bed reactor and a liquid separator. The temperature of the reactor was adjusted by a heat carrying oil circulation. The pressure and stream of hydrogen were controlled electronically. The aqueous HPA solution was pumped into the stream of hydrogen before the preheating station and the mixture was introduced at the head of the reactor (trickling bed procedure). After the mixture had passed through the reactor, the product obtained was removed from the separating vessel at regular intervals and the hydrogen was continuously recycled by means of a compressor.

The product was investigated for unreacted HPA by means of HPLC (high pressure liquid chromatography) and the 1,3-propanediol formed was determined by GC (gas chromatography).

The nickel comparison catalyst and a platinum catalyst to be used according to the present invention on pyrogenic titanium oxide charged with 2% of platinum in the form of extrusion moulded particles were investigated for their long-term performance with respect to conversion rate and selectivity. The concentration of HPA in the educt solution was in both cases 11% by weight.

Figure 2:
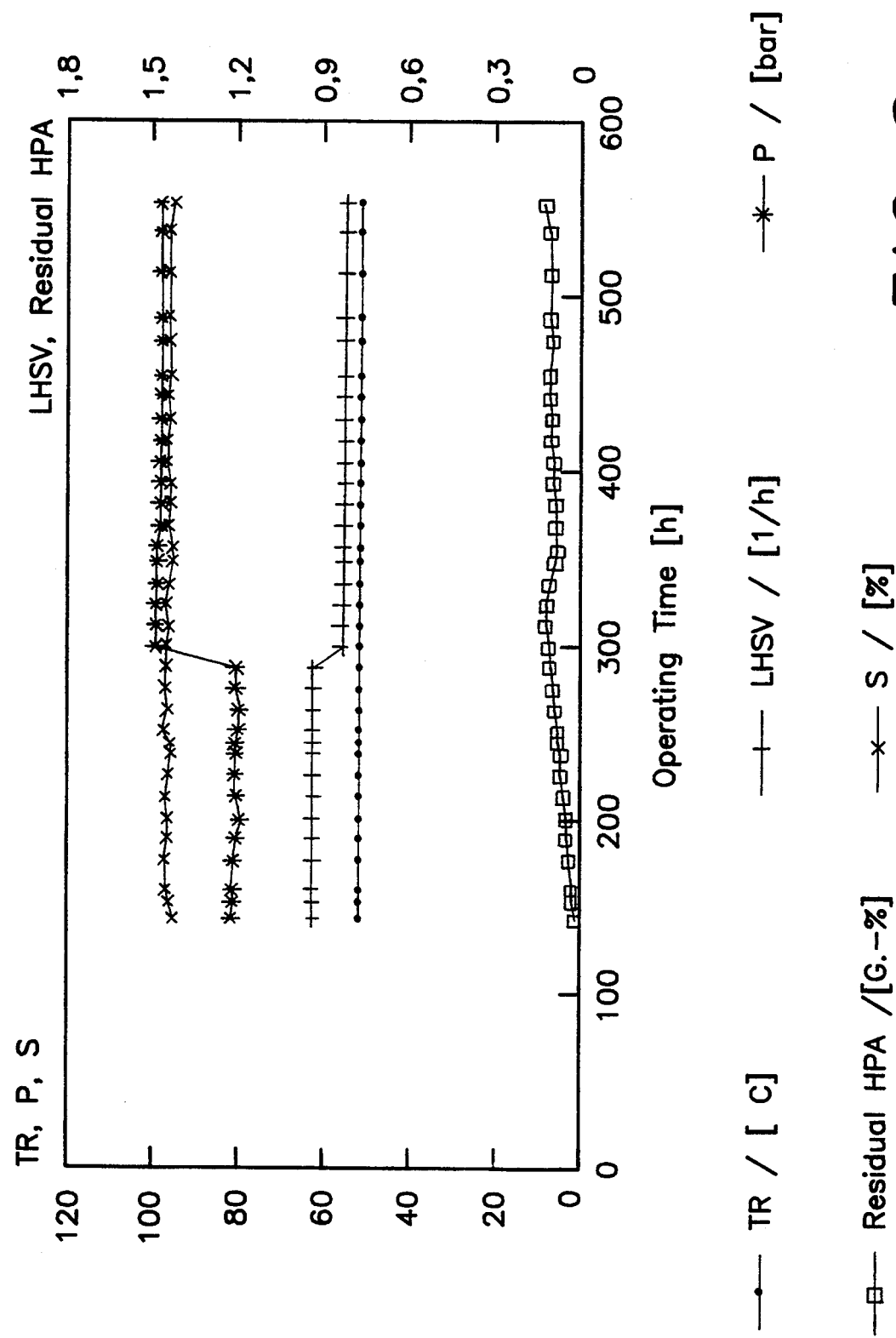
FIG. 2: Represents the long term performance of a comparison process using $Ni/Al_2O_3/SiO_2$ catalyst.

FIGS. 1 and 2 show the variation with time of the reaction temperature TR, the liquid hourly spaced velocity LHSV, the hydrogen pressure P, the residual HPA content of the product solution, and the selectivity S of hydrogenation in dependence upon the operating time for the process according to the invention using Pt/$TiO_2$ catalyst (FIG. 1 and Table 4) and for the comparison process using nickel catalyst (FIG. 2 and Table 5). As may be seen from the graphs of FIGS. 1 and 2, hydrogenation with the Pt/$TiO_2$ catalyst was carried out at a reaction temperature of 60° C., a hydrogen pressure of 90 bar and a liquid hourly space velocity of 0.85 $h^{-1}$; whereas in the case of the nickel catalyst a reaction temperature of 50° C. was employed and the process was started with a hydrogen pressure of 80 bar and a liquid hourly space velocity of 0.9 $h^{-1}$.

TABLE 4

(data for FIG. 1)

| Operating time (h) | Pressure (bar) | TR (°C.) | Residual HPA (Gew. %) | S (%) | LHSV (l/h) |
|---|---|---|---|---|---|
| 149.5 | 90 | 60 | 0.022 | | 0.8 |
| 172.5 | 90 | 60 | 0.022 | 98.6 | 0.814 |
| 196.5 | 90 | 60 | 0.022 | 98.8 | 0.81 |
| 220.5 | 90 | 60 | 0.024 | 99.1 | 0.81 |
| 238.5 | 90 | 60 | 0.025 | 99.2 | 0.81 |
| 262.5 | 90 | 60 | 0.027 | 98.3 | 0.81 |
| 286.5 | 90 | 60 | 0.029 | 98.5 | 0.818 |
| 310.5 | 90 | 60 | 0.034 | 101.5 | 0.818 |
| 334.5 | 90 | 60 | 0.032 | 102.5 | 0.818 |
| 358.5 | 90 | 60 | 0.033 | 102.4 | 0.81 |
| 302.5 | 90 | 60 | 0.033 | 103.1 | 0.81 |
| 406.5 | 90 | 60 | 0.03 | 101.6 | 0.8 |
| 430.5 | 90 | 60 | 0.033 | 101.5 | 0.8 |
| 454.5 | 90 | 60 | 0.034 | 101.5 | 0.82 |
| 478.5 | 90 | 60 | 0.029 | 99.6 | 0.81 |
| 502.5 | 90 | 60 | 0.028 | 100.65 | 0.800 |
| 526.5 | 90 | 60 | 0.029 | 98.8 | 0.81 |
| 550.5 | 90 | 60 | 0.034 | 97.2 | 0.808 |

TABLE 5

(data for FIG. 2)

| Operating time (h) | Pressure (bar) | TR (°C.) | Residual HPA (Gew. %) | S (%) | LHSV (l/h) |
|---|---|---|---|---|---|
| 149 | 81 | 50 | 0.03 | 96.1 | 0.917 |
| 155 | 80 | 50 | 0.04 | 97.2 | 0.917 |
| 161 | 81 | 50 | 0.04 | 97.8 | 0.917 |
| 179 | 81 | 50 | 0.05 | 98 | 0.917 |
| 191 | 80 | 50 | 0.06 | 97.2 | 0.917 |
| 203 | 79 | 50 | 0.06 | 97.5 | 0.917 |
| 215 | 80 | 50 | 0.07 | 98.2 | 0.917 |
| 227 | 80 | 50 | 0.08 | 97 | 0.917 |
| 239 | 80 | 50 | 0.08 | 96.5 | 0.917 |
| 245 | 80 | 50 | 0.09 | 96.0 | 0.917 |
| 253 | 79 | 50 | 0.09 | 98.5 | 0.917 |
| 265 | 79 | 50 | 0.1 | 96.8 | 0.917 |
| 277 | 80 | 50 | 0.11 | 97.9 | 0.917 |
| 289 | 80 | 50 | 0.12 | 97.5 | 0.917 |
| 301 | 100 | 50 | 0.12 | 97.5 | 0.81 |
| 313 | 100 | 50 | 0.13 | 96.9 | 0.81 |

TABLE 5-continued (data for FIG. 2)

| Operating time (h) | Pressure (bar) | TR (°C.) | Residual HPA (Gew. %) | S (%) | LHSV (l/h) |
|---|---|---|---|---|---|
| 325 | 100 | 50 | 0.13 | 97.9 | 0.81 |
| 337 | 99 | 50 | 0.12 | 97.7 | 0.81 |
| 349 | 99 | 50 | 0.1 | 96.1 | 0.81 |
| 357 | 100 | 50 | 0.08 | 95.9 | 0.81 |
| 369 | 99 | 50 | 0.09 | 97.8 | 0.81 |
| 381 | 99 | 50 | 0.09 | 98.9 | 0.81 |
| 393 | 99 | 50 | 0.1 | 96.8 | 0.81 |
| 405 | 99 | 50 | 0.1 | 97.6 | 0.81 |
| 417 | 99 | 50 | 0.11 | 97.5 | 0.81 |
| 429 | 99 | 50 | 0.1 | 97 | 0.81 |
| 441 | 99 | 50 | 0.11 | 97.6 | 0.81 |
| 453 | 99 | 50 | 0.11 | 96.8 | 0.81 |
| 473 | 99 | 50 | 0.1 | 97 | 0.81 |

The hydrogenation conditions were less favorable for the Pt/TiO$_2$ catalyst on account of the above-described doubling of the formation of by-product per 10° C. of rise in temperature. An outstandingly constant conversion rate was nevertheless obtained unexpectedly. (The residual HPA content remains constant.) The values of the selectivity S are in some cases over 100%. This is due to the fact that the organic impurities present in the educt solution from the hydration of acrolein are to some extent also converted into 1,3-propanediol.

When the nickel catalyst of FIG. 2 was used, a marked increase in the residual HPA was found after an operating time of only 200 hours. After about 290 hours, this proportion had increased to such an extent that it was necessary to lower it by reducing the liquid hourly space velocity from 0.9 h$^{-1}$ to 0.85 h$^{-1}$ and raising the hydrogen pressure of 100 bar.

Further variations and modifications of the foregoing will be apparent to those skilled in the art and such variations and modifications are attended to be encompassed by the claims that are appended hereto.

What is claimed is:

1. A process for the preparation of 1,3-propanediol, said process comprising hydrogenating hydroxypropionaldehyde (HPA) in aqueous solution in the presence of a formed carrier catalyst in a fixed bed, said hydrogenating being carried out at temperatures of from 30° to 180° C. and hydrogen pressures of from 5 to 300 bar and at a pH of from 2.5 to 6.5, wherein said carrier catalyst consists essentially of titanium oxide on which platinum is applied in a finely divided form in a quantity of from 0.1 to 5.0% by weight based on the carrier.

2. The process according to claim 1, wherein said titanium oxide is a pyrogenic titanium oxide obtained from titanium tetrachloride by flame hydrolysis and having a specific surface area of from 40 to 60 m$^2$/g, a total pore volume of from 0.25 to 0.75 ml/g, an average primary particle size of 20 nm, a density of 3.7 g/cm$^3$, an X-ray structure of 20 to 40% rutile and 80 to 60% anatase, and impurities of silicon dioxide, aluminum oxide and iron oxide amounting to less than 0.5% by weight.

3. The process according to claim 2, wherein said catalyst carrier is impregnated with the required quantity of platinum, using a soluble platinum compound, and is then dried and reduced in a stream of hydrogen over a period of from 1 to 10 hours at temperatures of from 250° to 500° C.

4. The process according to claim 3, wherein said platinum metal is finely divided in the catalyst carrier, with crystallite sizes of from 1 to 10 nm, and its carbon monoxide adsorption is from 0.5 to 1.6 ml of CO/g of catalyst.

5. The process according to claim 3, wherein said platinum compound is selected from the group consisting of tetraaminoplatinum(II) nitrate, tetraaminoplatinum(II) hydroxide, tetraaminoplatinum(II)-chloride-1-hydrate, and hexachloroplatinic acid.

6. The process according to claim 5, wherein said platinum compound is hexachloroplatinic acid.

7. The process according to claim 1, wherein said titanium oxide is a pyrogenic titanium oxide obtained from titanium tetrachloride by flame hydrolysis and tempered at a temperature above 600° C., wherein said titanium oxide has a specific surface area below 13 m$^2$/g and a rutile X-ray structure.

8. The process according to claim 1, wherein the concentration of the HPA in said solution is at least 5% by weight.

9. The process according to claim 1, wherein said 1,3-propanediol is free of platinum.

10. A method for the preparation of 1,3-propanediol, said method comprising contacting an aqueous solution of hydroxypropionaldehyde (HPA) with a formed carrier catalyst in a fixed bed consisting essentially of titanium oxide on which platinum is applied in a finely divided form in a quantity of from 0.1 to 5.0% by weight based on the carrier, wherein said titanium oxide is a pyrogenic titanium oxide obtained from titanium tetrachloride by flame hydrolysis and having a specific surface area of from 40 to 60 m$^2$/g and a total pore volume of from 0.25 to 0.75 ml/g, which titanium oxide has an average size of primary particles of 20 nm, a density of 3.7 g/cm$^3$ and an X-ray structure of 20 to 40% rutile and 80 to 60% anatase, its impurities, composed of silicon dioxide, aluminum oxide and iron oxide, amounting to less than 0.5% by weight; said contacting being carried out at temperatures of from 30° to 180° C. and hydrogen pressures of from 5 to 300 bar and at a pH of from 2.5 to 6.5.

11. The process according to claim 10, wherein the concentration of the HPA in said solution is at least 5% by weight.

12. A method for the preparation of 1,3-propanediol, said method comprising contacting an aqueous solution of hydroxypropionaldehyde (HPA) with a formed carrier catalyst in a fixed bed consisting essentially of titanium oxide on which platinum is applied in a finely divided form in a quantity of from 0.1 to 5.0% by weight based on the carrier, wherein said titanium oxide is a pyrogenic titanium oxide obtained from titanium tetrachloride by flame hydrolysis and tempered at a temperature above 600° C., wherein said titanium oxide has a specific surface area below 13 m$^2$/g and a rutile X-ray structure; said contacting being carried out at temperatures of from 30° to 180° C. and hydrogen pressures of from 5 to 300 bar and at a pH of from 2.5 to 6.5.

13. The process according to claim 12, wherein the concentration of the HPA in said solution is at least 5% by weight.

* * * * *